(12) United States Patent
Markovsky et al.

(10) Patent No.: US 6,319,466 B1
(45) Date of Patent: Nov. 20, 2001

(54) TEST DEVICE FOR DETECTING THE PRESENCE OF A RESIDUE ANALYTE IN A SAMPLE

(75) Inventors: Robert J. Markovsky, Amesbury; Cheryl A. Boyer, Malden; Stanley E. Charm, Boston; Paul R. Donahue, Southboro, all of MA (US); Yael Agi Glickman, Moshav Tsofit (IL); Steven J. Saul, Arlington, MA (US); Joan L. Scheemaker, Chelmsford, MA (US); Richard T. Skiffington, North Reading, MA (US); Shefali B. Trivedi, Quincy, MA (US); Eliezer Zomer, Newton, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

(21) Appl. No.: 09/118,135

(22) Filed: Jul. 16, 1998

Related U.S. Application Data

(63) Continuation-in-part of application No. 09/001,775, filed on Dec. 31, 1997, now Pat. No. 5,985,675.
(60) Provisional application No. 60/052,644, filed on Jul. 16, 1997, and provisional application No. 60/088,987, filed on Jun. 11, 1998.

(51) Int. Cl.[7] .................. G01N 21/78; G01N 33/551; G01N 33/553; G01N 33/558; G01J 8/20

(52) U.S. Cl. ................. 422/56; 422/57; 422/58; 422/61; 422/187; 422/188; 436/514; 436/524; 436/525

(58) Field of Search .................. 436/514, 518, 436/524, 525, 538; 422/56, 57, 58, 61, 187, 188

(56) References Cited

U.S. PATENT DOCUMENTS

| 4,703,017 | 10/1987 | Campbell et al. | 436/501 |
| 4,743,560 | 5/1988 | Campbell et al. | 436/501 |

(List continued on next page.)

FOREIGN PATENT DOCUMENTS

| 0279574 A1 | 8/1988 | (EP) . |
| 0 291 194 B1 | 11/1988 | (EP) . |

(List continued on next page.)

OTHER PUBLICATIONS

Brady et al., Journal of Food Protection, 56(3):229–233, Mar. 1993.*

(List continued on next page.)

Primary Examiner—Brenda Brumback
(74) Attorney, Agent, or Firm—Leslie Meyer-Leon, Esq.; IP Legal Strategies Group P.C.

(57) ABSTRACT

A test device for detecting the presence of a residue analyte in a sample includes a support strip and a sample-absorbing matrix attached to the support strip. The sample-absorbing matrix has a material for absorbing an amount of the sample. The test device also includes a mobile-phase support for holding a mobile-phase composition. The mobile-phase support is attached to the support strip and in contact with the sample-absorbing matrix. A mobile-phase composition is disposed on the mobile-phase support and has a receptor for binding with the analyte. The mobile-phase composition can be carried in the sample. A stationary-phase membrane is attached to the support strip and has a first membrane end in contact with the mobile-phase composition and a second membrane end. The membrane allows lateral capillary flow of the sample from the first membrane end to the second membrane end. A test zone is on the stationary-phase membrane between the first membrane end and second membrane end and having a first binder for binding with an unbound receptor. A control zone is the stationary-phase a membrane between the test zone and second membrane end and has a second binder for binding with an analyte-bound receptor or residual unbound receptor.

33 Claims, 6 Drawing Sheets

U.S. PATENT DOCUMENTS

| | | | |
|---|---|---|---|
| 4,999,285 | 3/1991 | Stiso | 435/7.9 |
| 5,238,652 | 8/1993 | Sun et al. | 422/61 |
| 5,266,497 | 11/1993 | Imai et al. | 436/514 |
| 5,451,504 | 9/1995 | Fitzpatrick et al. | 435/7.2 |
| 5,591,645 | 1/1997 | Rosenstein | 436/514 |
| 5,602,040 | 2/1997 | May et al. | |
| 5,622,871 | 4/1997 | May et al. | 436/514 |
| 5,656,448 | 8/1997 | Kang et al. | |
| 5,714,389 * | 2/1998 | Charlton et al. | 436/514 |
| 5,739,041 | 4/1998 | Nazareth et al. | |
| 5,753,517 | 5/1998 | Brooks et al. | 436/514 |
| 6,001,658 | 12/1999 | Fredrickson | |

FOREIGN PATENT DOCUMENTS

| | | |
|---|---|---|
| 0299428 A2 | 1/1989 | (EP) . |
| 0306336 A2 | 3/1989 | (EP) . |
| 0321145 A2 | 7/1989 | (EP) . |
| 378 391 * | 7/1990 | (EP) . |
| 0 291 176 B1 | 11/1991 | (EP) . |
| 0 582 231 A1 | 2/1994 | (EP) . |
| 0 284 232 B1 | 6/1995 | (EP) . |
| WO 90/15327 | 12/1990 | (WO) . |
| WO 94/02850 | 2/1994 | (WO) . |
| WO 96/38720 | 12/1996 | (WO) . |
| WO 97/03209 | 1/1997 | (WO) . |
| WO 97/05287 | 2/1997 | (WO) . |

OTHER PUBLICATIONS

Charm et al., Journal of the Association of Food and Drug Officials, 58(1), 17–29, Jan. 1994.*

Charm, et al., J. Assoc. Off. Anal. Chem., 71(2), 1988.*

Hassnoot et al., "Evaluation of a Sol Particle Immunoassay (SPIA) Based Single–Step Strip Test for the Detection of Sulfadimidine Residues", Euro Residue III (1996) 461–465.

Verheijen et al., "Single–Step Strip Tests for Residue Analyses", DLO–State Institute for Quality Control of Agricultural Products (RIKILT–DLO) (Jun. 3, 1998).

* cited by examiner

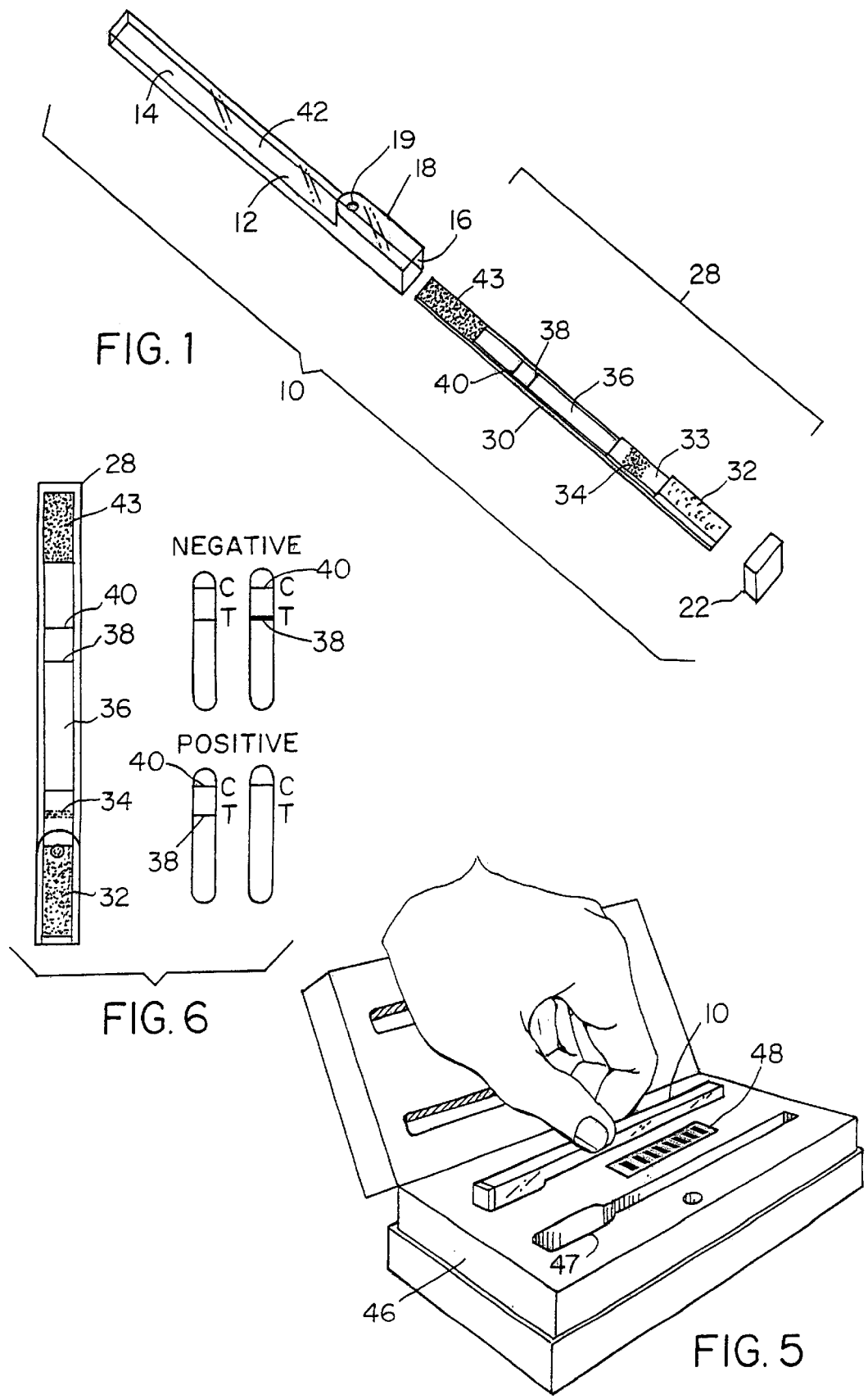

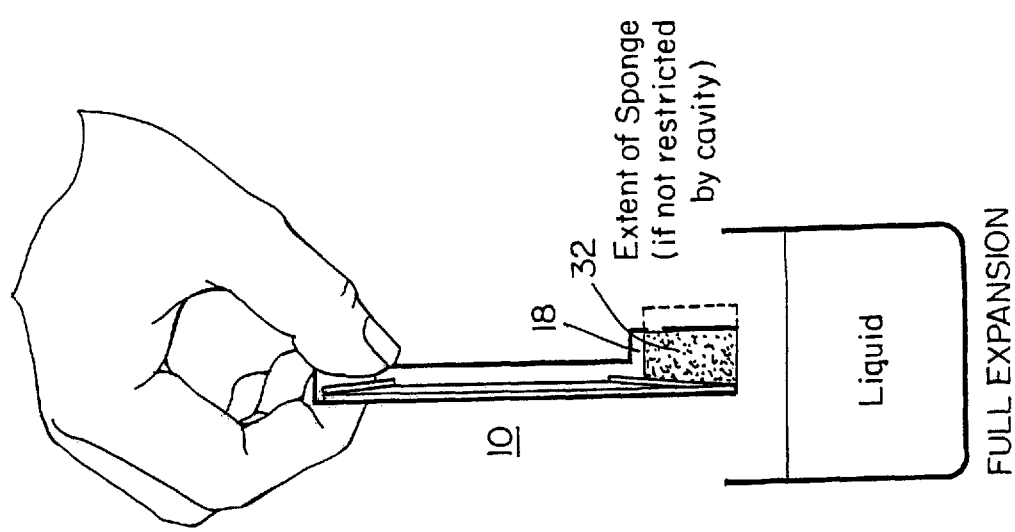
FIG. 4 FULL EXPANSION
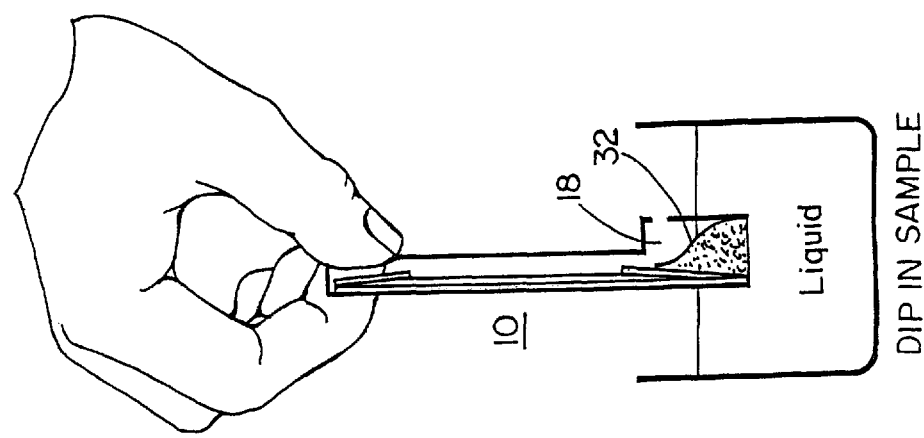
FIG. 3 DIP IN SAMPLE
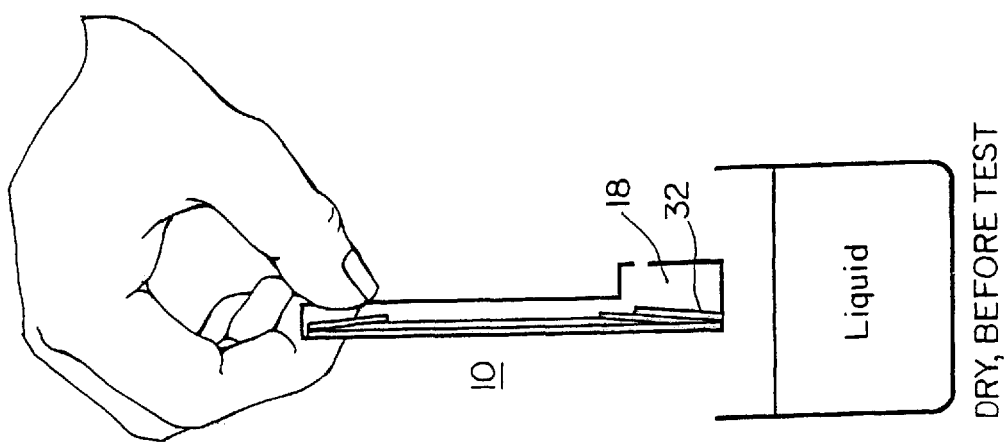
FIG. 2 DRY, BEFORE TEST

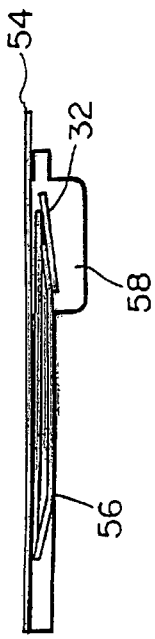
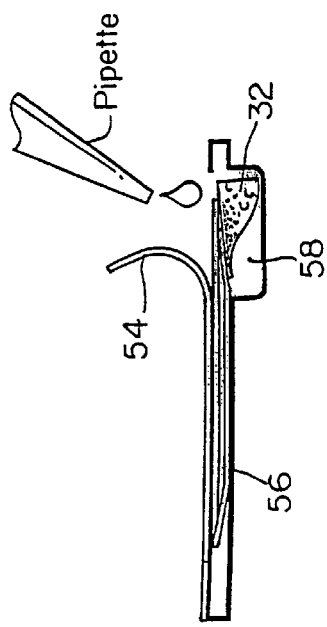
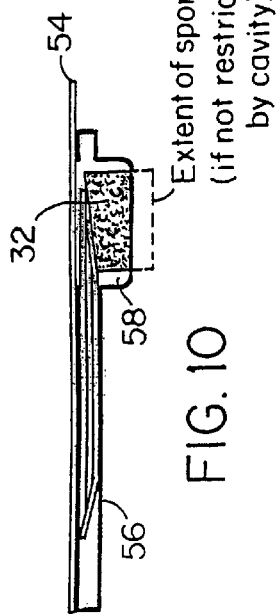
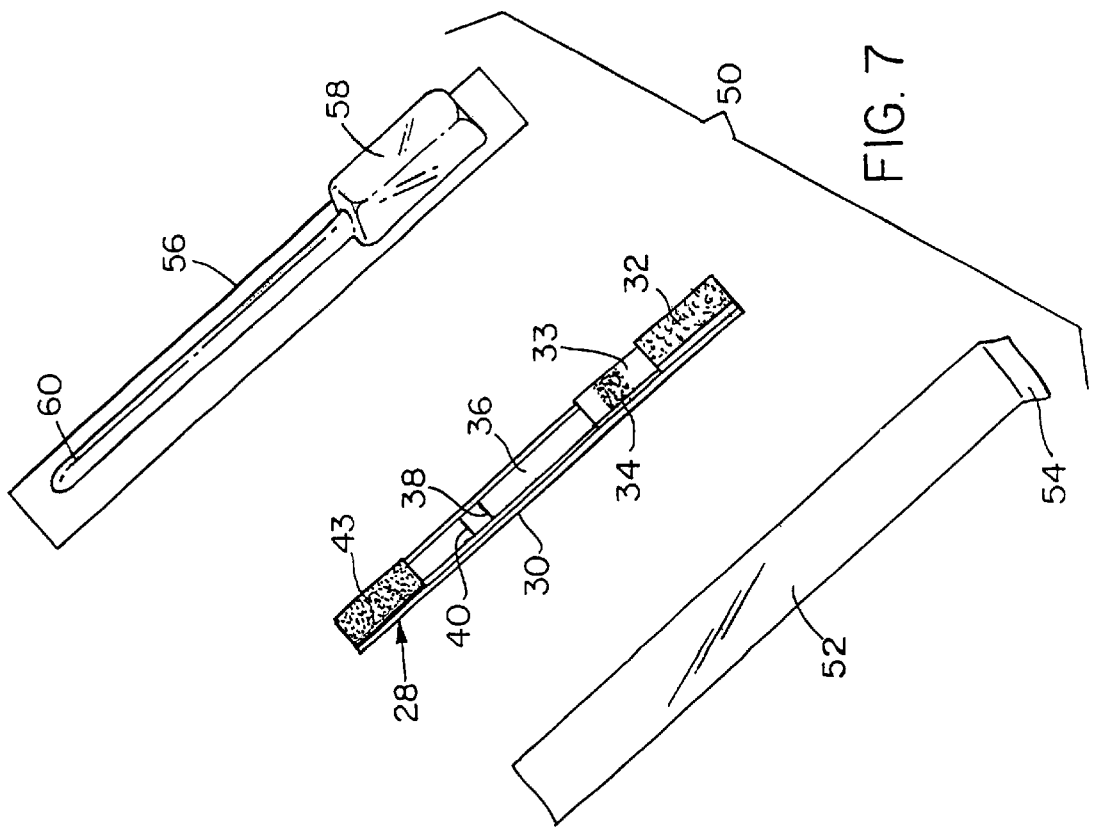

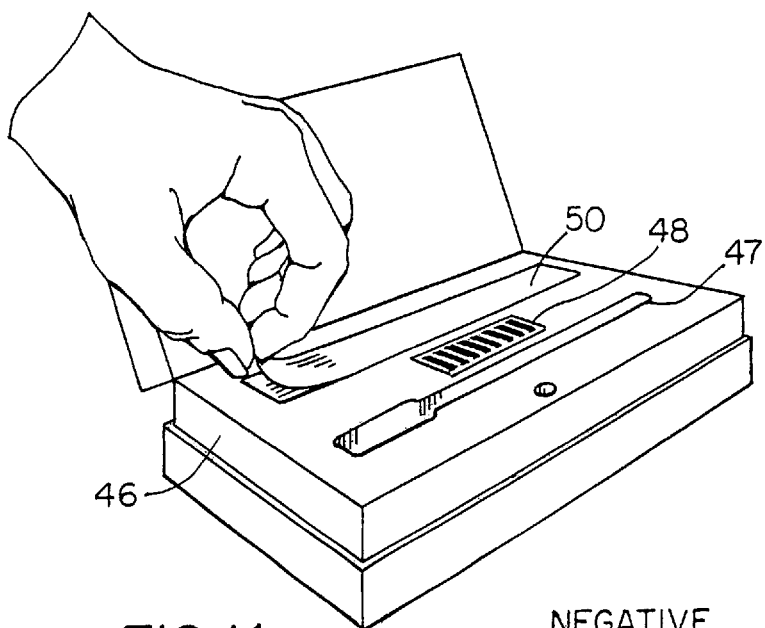
FIG. 11
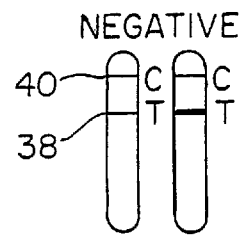
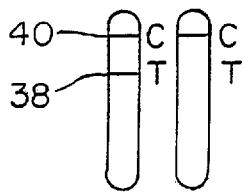
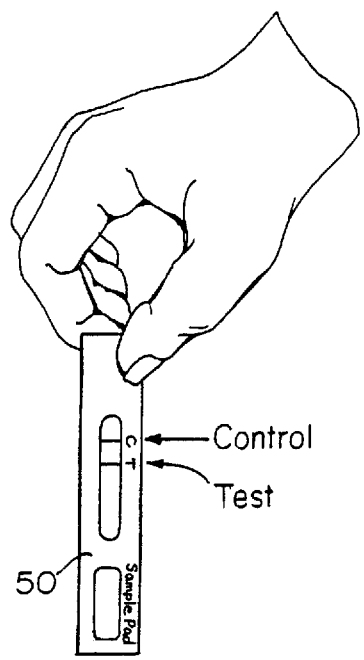
FIG. 13
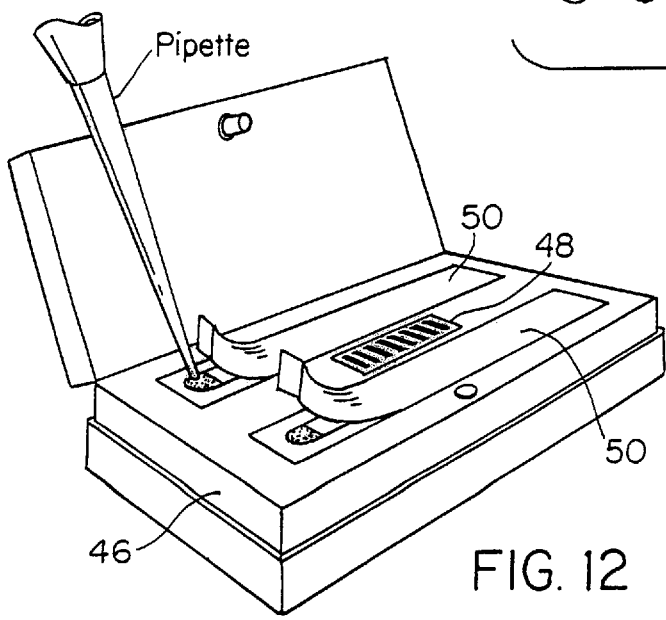
FIG. 12

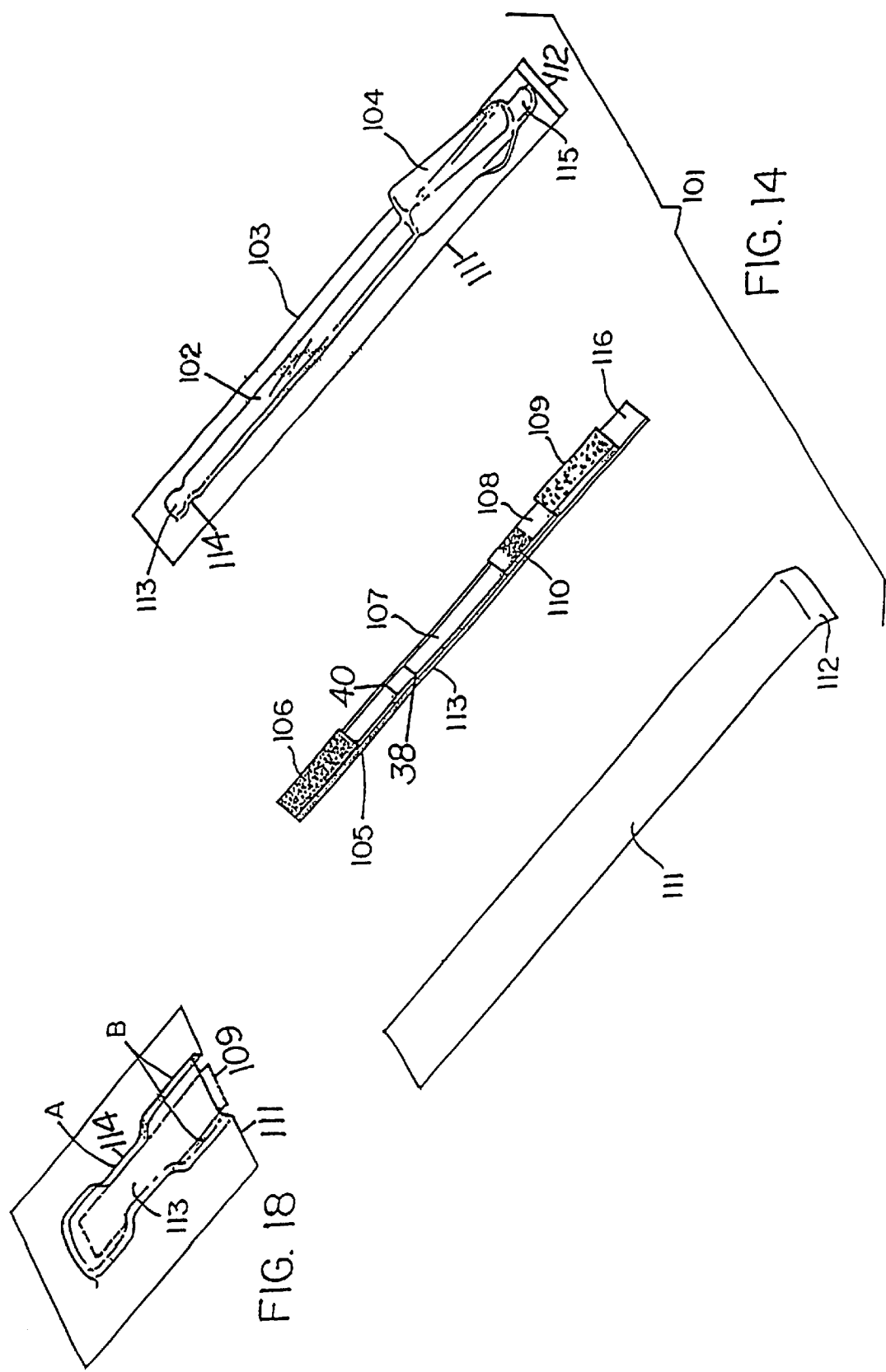

TEST DEVICE FOR DETECTING THE PRESENCE OF A RESIDUE ANALYTE IN A SAMPLE

RELATED APPLICATIONS

The present application claims the benefit of U.S. Provisional patent Application Ser. No. 60/052,644, filed on Jul. 16, 1997, and Ser. No. 60/088,937, filed on Jun. 11, 1998. The contents of each provisional application are incorporated herein by reference in their entirety. The present application is a continuation-in-part of co-pending U.S. patent application Ser. No. 09/001,775, filed on Dec. 31, 1997 now U.S. Pat. No. 5,985,675, the teachings of which are incoporated herein by reference in their entirety.

BACKGROUND OF THE INVENTION

Lateral-flow or immunochromatographic test kits and methods for the detection of the presence or concentration of chemical residues or analytes or classes thereof from liquid samples have been developed. An example of one such test kit includes a pregnancy test kit.

Particularly in the food safety area it has long been recognized that residue detection should be accurate, inexpensive and easily conducted. Consumers and governments are becoming increasingly aware of the necessity for testing foods for the presence of undesirable residues naturally occurring or otherwise.

Since a large portion of the consumers are children, food safety has long been critical in the dairy industry. Antibiotic residues used on a dairy farm occasionally appear in the milk supply. The hazards associated with these undesirable residues, include allergic reactions, assisting the propagation of new and sometimes drug resistant microorganisms and other long term health risks.

Government agencies have established in some cases legal limits for particular residues in foods, for example antibiotic residues in milk. Residues above the "legal" limit are considered unsafe for human consumption. Residue levels below the legal limit are considered "safe". It is important, therefore, that detection methods, in addition to being inexpensive and easily conducted, do not give positive results when residues are below legal limits so that otherwise acceptable milk, or other foods, are not discarded or otherwise treated as containing residues above legal limits.

SUMMARY OF THE INVENTION

The invention relates to an analyte or chemical residue test device and method employing a lateral-flow test strip for the detection of the analyte or residue in a sample and a method therefor.

Often a liquid, such as milk, has one or more contaminants or analytes that are in trace amounts that need to be assayed. In order to detect the analyte, the present invention employs a labeled receptor that reacts with the analyte to form an analyte-receptor complex. The labeled receptor is positioned within or proximate to a membrane and when exposed to the liquid, lateral capillary flow occurs thereon. In the flow, the liquid carries the analyte-receptor complex, and any unbound labeled receptor with it. Positioned on the membrane in the flow path is a test zone. The test zone has a representative analyte conjugate attached to the membrane, to bind unbound receptor to form a first analyte conjugate receptor complex that, as a result of the label, has a signal visible to the eye or readable with an instrument.

Capillary flow of the liquid continues on the membrane to a control zone. The control zone includes a binder attached to the membrane that binds with the labeled receptor. Upon binding, the control zone changes to a signal that can be visible to the eye or readable with an instrument or visible under special light conditions, such as ultraviolet. If the signal in the test zone is more intense than the signal in the control zone, the test indicates that the analyte is not present in a sufficient amount (a negative test). If the test zone signal is less intense than the control zone signal, the test indicates that the analyte is present in an amount in excess of allowable levels (a positive test).

The receptor may bind a family of analytes (one or a plurality of analyte) which have similar structural binding sites. Members of an analyte family can have different detection level requirements and, therefore, additional analyte binders can be employed, for example, monoclonal or polyclonal antibodies, that bind a portion of the analyte in competition with the receptor, in the sample, thereby decreasing test sensitivity. The antibodies are mixed with the labeled receptor in an amount to adjust the sensitivity for a specific analyte or group of analytes. The sensitivity of the test is adjusted so that a positive test result is not given unless a certain threshold of analyte is present in the sample.

The test device includes a support strip and a sample-absorbing matrix attached to the support strip. The sample-absorbing matrix is a material for absorbing an amount of the sample for example a sponge. The test device also includes a mobile-phase support for holding a mobile-phase composition. The mobile-phase support is attached to the support strip and is in contact with the sample-absorbing matrix. A mobile-phase composition is disposed within or on the mobile-phase support and has a labeled receptor for binding with the analyte. The mobile-phase composition can be carried in the sample and flow together with the sample. A stationary-phase membrane is attached to the support strip and has a first membrane end in contact with the mobile-phase composition and a second membrane end in contact with the disposal zone. The membrane allows lateral capillary flow of the sample from the first membrane end to the second membrane end. A test zone is on the stationary-phase membrane between the first membrane end and second membrane end and has an analyte conjugate for binding with unbound labeled receptor. A control zone is on the stationary-phase membrane between the test zone and second membrane end and has a binder, for example an antibody to the particular receptor, for binding with analyte-bound receptor and excess unbound receptor.

The invention also includes an analyte test device for detecting, in a general horizontal position, an analyte in a liquid sample by capillary lateral flow in a chromatographic test strip. The device includes an elongated housing defining an elongated strip cavity having an open application aperture at one end and having another end. The cavity is adapted to receive and hold a test strip therein. The housing has a transparent top cover section to allow the observation of tests results on the test strip. The housing is characterized by an enlarged application cavity extending outwardly from the top cover and having or adapted to have an open end at the application end. The test device includes a test strip positioned in the strip cavity.

The test strip includes a support strip with a plurality of sequential contacting, liquid-sample, permeable zones extending from the first end to the second end. The zones allow the lateral capillary flow of the liquid sample from the first end to second end. The zones include a sample-absorbing and filtering zone composed of an expandable, porous, compressed-material layer which moves, on contact with the liquid sample, between a nonexpanded state to an expanded state on absorption of a preselected amount of the liquid sample, and a mobile phase support having a mobile-phase composition layer thereon or therein with a labeled receptor for binding the analyte in the liquid sample thereon, typically a visible area containing colored beads and a membrane generally of nitrocellulose which includes a reaction zone having at least one stationary analyte conjugate reference or test line, or generally a test and a separate control line thereon and optionally a disposal zone of liquid-sample absorbent material to absorb less liquid sample and to aid in capillary flow to the second end.

The sample-absorbing zone with the compressed material layer is positioned adjacent the application cavity. The compressed-material layer and the application cavity are designed to allow the compressed-material layer to absorb a selected amount of liquid sample for testing and in an amount sufficient to carry out the test and to expand from a dry, nonexpanded form to a wet, expanded state. The material layer in a wet, expanded state fills substantially the application cavity and causes sufficient pressure on the housing walls of the expansion cavity to drive capillary flow of the liquid sample in the application cavity to a selected volume, when the open application end of the test device is inserted into a liquid to obtain the liquid sample or when a known amount of sample is pipetted into the application cavity.

In one embodiment, a housing is employed, such as a one-piece, integral, injection-molded, all-transparent, plastic material, with the plastic material selected or designed to be subject to incubator temperatures of 30° C. or more for incubation times, for example, 2 to 10–15 minutes, depending on the particular test although not all tests will require incubation at temperatures other than room temperature.

In one embodiment, the housing includes a generally toothbrush shape, with an enlarged, generally triangular, toothbrush-type head at the open application end of the housing, with a dry, inert, porous, expanded, liquid-permeable, absorbing material in a generally triangular layer as an absorbing zone in the test strip, for example, of cellulose or nitrocellulose, positioned beneath the open bottom of the application cavity or chamber. The absorbing layer on contact, such as immersion of the application end of the housing of the test device in a liquid, absorbs a preselected amount of the liquid sample necessary for the test. The absorbing-layer material expands for example, in one to thirty seconds, to fill or substantially fill the expansion cavity and contact the surrounding walls of the expansion-cavity housing, to cause sufficient pressure within the expansion cavity and the expanded state of the material to drive capillary flow laterally in the underlying test strip laterally toward the end of the elongated housing where the test strip is positioned. The expansion cavity and underlying absorbing-layer material which generally mimics two dimensions of the expansion cavity, permit absorbing and filtering of the selected amount of liquid sample for the test strip. The expansion cavity and absorbing-layer material aid in driving the lateral flow of the liquid sample in the test strip in the housing toward the disposal zone at the end of the strip to receive the liquid sample where employed. If the absorbing layer does not expand sufficiently to fill or substantially fill the expansion cavity, the lateral or capillary flow rates and times can be unsatisfactory. The flow rate can be too slow and the time period can be too long. If the absorbing layer is used in excess, then excess pressure occurs in the expansion cavity, and the expanded absorbing layer tends to retard the desired lateral flow of the liquid sample.

The housing with the toothbrush-shaped design can include a separate injection-molded housing with an optional end cover, to protect the exposed application end before sampling and after sampling, and in the incubation chamber, to prevent cross-contamination from other sources. The test device with the molded housing allows the user to handle the handle end of the housing and to obtain a liquid sample merely by dipping the open application cavity into a liquid.

The housing can include a toothbrush-shaped design, wherein the expansion cavity is formed in a plastic, usually transparent, blister-type package which is sealed against a flat support, such as a paper strip or another plastic strip, and which encompasses within the blister package the selected test strip. The blister package includes a removable seal strip at the one application end of the enclosed test strip, for peeling or removal prior to use and for the introduction of a selected volume of the liquid to the application-absorbing zone of the test strip while in the blister package, e.g. by pipetting. The blister package with the liquid sample and test strip can be incubated in the incubator and the test results observed visually or read by an instrument.

In another embodiment, it has been discovered to be desirable to provide one or more apertures in the housing which defines the expansion cavity, to permit the time-controlled and more rapid absorbing of the liquid sample into the absorbing material for more efficient absorption and to reduce absorption time of the liquid sample. In particular, one or more apertures should be placed on the top cover or surface of the expansion-cavity housing, particularly of the molded housing, rather than on the sides, so that entrapped air after immersion is discharged from the expansion cavity, as the absorbing layer expands into the wet, absorbing, expanded state. While a flat, rectangular strip of absorbing material is shown with a generally rectangular expansion cavity which mimics and provides for the expanded, rectangular strip of the absorbing zone, it is recognized that the size, material, dimensions and shape of the absorbing material and the shape or form of the expansion cavity may vary in the practice of the invention. Typically, the open bottom of the expansion cavity is directly above the absorbing layer and usually of about the same width and length dimensions, to permit expansion without restriction of the absorption layer into the expansion cavity.

While a fully transparent top cover is desirable to enclose the test strip and observe or read the test results on the test strip, it is recognized that the top cover can be open or have an aperture to view the test results, or only a section of the top cover be transparent to view the test results, or where applicable the housing may be modified, so that the test results can be determined by optical or electronic instrument means.

The test device can be packaged for use in a blister-type package or employ a fixed or slidable protective cap at the application end, to protect the test device from contamination prior to use and to protect the test device after contact with the liquid sample and in the incubator (where required in the test), to protect against cross-contamination. The protective cap can be removable and enclose totally the application end of the housing, or merely be slidably extended outwardly from the application end between a retracted use position and extended, protective, closed position.

The test device employs a test strip selected to detect the presence or concentration of selected analytes or residues, either a single residue or classes thereof, and visually by reference of a reaction test zone or reference line in the test strip which may be observed or measured. Usually, a control zone or line is spaced apart slightly downstream from the reference zone or lines for control purposes. The housing of the test device is applicable to a wide variety of present employed or described test strips which are based on lateral flow or capillary flow, regardless of the nature of the particular analyte-residue test, provided only that the application or liquid contact portion of the test strip requires or uses a filtering absorbing material which moves by liquid-sample contact between a nonexpanded and an expanded state at or toward the one application end of the test device. Typically, the test strip has a support and includes on one surface a plurality of contacting, liquid-permeable, sequential zones or sections with a stationary zone, a mobile zone and, optionally, a disposal zone. The test device is particularly useful in connection with the liquid sample comprising a fluid, for example, urine, blood, milk or corn extract and in the detection of antibiotics, like beta lactams, toxins, viruses, bacteria, pesticides and the like. However, the test device can employ one or more test strips directed to a variety of tests.

Where applicable, the test device is employed in combination with an incubator, such as a portable, electrically heated incubator with an incubation chamber which can be dimensioned to receive the test-device housing snugly therein for heating for a selected incubator time, for example, at a temperature in the range of between about 45 and 75° C., preferably between 55 to 65° C., and for a period of 1 to 10–15 minutes. The test device and incubator also include a timer, so that the incubation period can be timed by a user.

In operation, the test device with a protective covering or cap has the cover or cap removed and the application end contacted with a liquid to be tested, such as by immersion, for about one to ten seconds and then removed, or a liquid sample pipetted into the application end. The absorbing material is allowed to expand within the expansion cavity, for example one to fifteen seconds, then the test device is placed in an incubator for a time period, then removed and the test results observed or measured. If the sample is pipetted the device is placed in the incubator and the sample is pipetted into the sample cavity.

The present invention includes many advantages such as combining high purity broad spectrum receptors or antibodies with high specific activity per surface area combined with counteracting residue specific antibodies (e.g. monoclonal) to achieve residue detection on the order of parts per billion (ppb) ($10^{-9}$) or parts per trillion (ppt) ($10^{-12}$) levels at or close to regulatory requirements. Targeting the active moiety of the chemical residue allows detection of a broad spectrum of active pharmaceuticals (e.g. veterinarian drugs, agricultural chemicals (e.g. pesticides), or microbial toxins and their active metabolites.) Further, additional antibodies can be added to adjust the threshold sensitivity of the test.

Other advantages include that all components can be incorporated in the device and reagent preparation is not necessary. The device is a one-step assay that does not require timing (results are stable from about four minutes to few hours). The device which has a built-in negative control eliminates the need for external control standards.

BRIEF DESCRIPTION OF THE DRAWINGS

FIG. 1 is a perspective, exploded view of a molded-housing test device.

FIGS. 2, 3 and 4 are schematic, illustrative view of the use of the test device of FIG. 1.

FIG. 5 is a perspective view of an incubator and the test device with a liquid sample.

FIG. 6 is an enlarged, front-plan view of the test strip of FIGS. 1–5, with enlarged, front, sectional views of positive and negative test results.

FIG. 7 is a perspective, exploded view of a blister-pack test device.

FIGS. 8,9 and 10 are schematic, illustrative, side views of the use of the test device of FIG. 7.

FIGS. 11 and 12 are perspective views of an incubator and the test device with a liquid sample.

FIG. 13 is an enlarged, front-plan view of the test strip of FIGS. 7–12, with enlarged, front, sectional views of positive and negative test results.

FIG. 14 is a perspective, exploded view of a blister-pack test device with protruding backing and narrowing of blister to produce pinch points.

FIG. 18 is an enlarged view of the strip movement restriction zone 114.

DETAILED DESCRIPTION OF THE INVENTION

Figure 15:
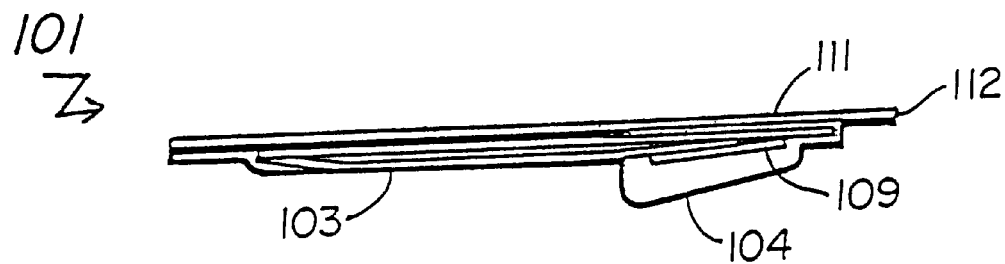
FIGS. 15,16 and 17 are schematic, illustrative, side views of the use of the test device of FIG. 14.
Figure 16:
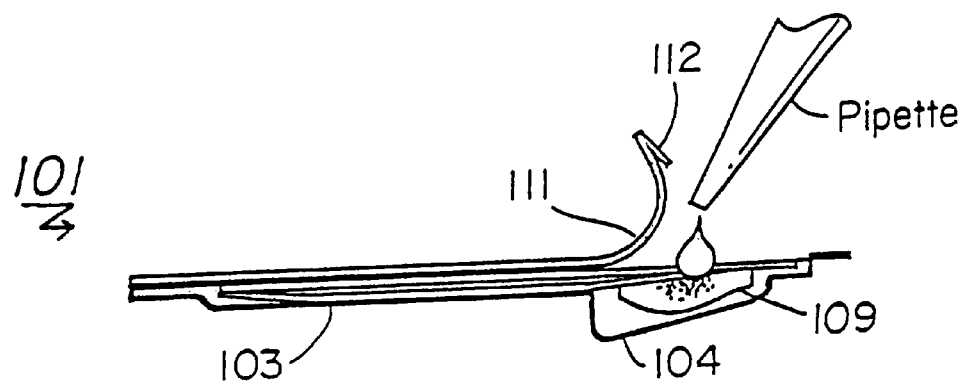

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. All percentages and parts are by weight unless otherwise indicated.

The present invention relates to a test device and method for detecting the presence of a residue analyte in a sample. The test and device use direct color, fluorescence or infrared recognition-based broad spectrum assays to rapidly detect low part per billion (ppb) presence of a chemical or a family of chemical residues sharing common recognition sites. The kits are designed for testing antibiotics, toxins and pesticides in food or environmental samples in the field, or in the lab. The assays are non-competitive using saturation chemistry.

In the drawings, FIGS. 1–6 show analyte test device 10 which includes elongated, molded housing 12. Housing 12 can be formed of a one-piece, injection-molded, transparent styrene polymer. Housing 12 defines elongated housing cavity 14 with open end 16, and having enlarged, rectangular application expansion cavity 18 at open end 16 of housing 12. Housing 12 includes an elongated bottom cavity formed during the injection-molding process. The housing includes an optional removable, friction-fitted or snap-on protective cap 22 adapted to fit over open end 16 of housing 12 and liquid expansion apertures 19 in the top cover of the application housing cavity to increase the efficiency of expansion of a sample-absorbing matrix, such as sponge 32, within the test time.

Housing cavity 14 includes therein on the bottom surface a lateral-flow test strip 28 adapted to detect the presence of an analyte in a liquid sample, such as milk. Test strip 28 includes support strip 30 with sponge 32 attached at one end. Sponge 32 can include a plurality of sequential layers comprising a rectangular pad of dry, compressed, cellulosic material as a liquid-sample absorbent secured to the face surface of the support strip 30. Sponge 32 is selected to expand in contact with the liquid, such as milk, to fill the expansion cavity 18 which sponge 32 mimics in two dimensions. For example, with milk, sponge 32 is about 3–4 mm by 12–14 mm, while cavity 18 is about 5–6 mm by 15–16 mm by 4–6 mm in height. Expansion cavity 18 can be dimensioned about 60% to 30% less than the full expansion of the sponge material.

Support strip 30 includes treated, mobile-phase support 33 with mobile-phase composition 34, stationary-phase membrane 36 which includes test zone 38 and control zone 40 for the analyte to be detected, and disposal zone 43 at second end of support strip 30 to capture excess liquid sample. Housing 12 includes transparent top cover 42 for visual observation of test zone (reference zone) 38 and control zone 40. Test strip 28 is placed and positioned loosely in the elongated cavity 14, with sponge 32 positioned beneath the expansion cavity 18, and sponge 32 extending generally to about or slightly beyond the plane of the open application end, and the end covered prior to use by protective cap 22.

In operation, protective cap 22 is removed prior to use and the open application end of housing 12 inserted briefly (about one to ten seconds) in the liquid, such as milk, to be tested employing elongated housing 12 as a handle. See FIG. 2. Test device 10 is removed and sponge 32 is allowed to expand to fill expansion cavity 18 and to start 5 the lateral flow of the milk sample through test strip 28 (2 to 6 minutes). See FIGS. 3 and 4. Preferably, protective cap 22 is inserted to protected against cross-contamination, and test device 10 then placed in a horizontal position, with the application cavity 18 extending downwardly in an electric-heated incubator 46 with incubator cavity 47 shaped to receive the test device, and incubation carried out, for example, for three to ten minutes. The incubation temperature is observed through the temperature-indicator scale 48. See FIG. 5. Incubated test device 10 is then removed and reversed, and the front view of the test device with test zone 38 and control zone 40 observed. See FIG. 6. The line readings for positive and negative controls are illustrated in FIG. 6 adjacent the front view of test device 10. In sponge 32, expansion is controlled by the expansion cavity 18 volume and size, resulting in sponge 32 completely filling expansion cavity 18 with a preselected volume of liquid, for example 0.1 to 1.0 ml, so the amount of liquid sample taken in for the test is controlled to the correct amount. The dimensions of expansion cavity 18 prevent the sponge pad 32 to fully expand, so that pressure is maintained in the expanded sponge, as shown in FIG. 4, to aid in forcing capillary-lateral flow of the liquid sample through the test strip 28 in the housing 12.

The drawings in FIGS. 7–13 illustrate another embodiment of test device 50 in a transparent blister package which includes transparent-tape plastic seal strip 52 with peel tag 54 at one end, and transparent blister package 56 adhesively secured to strip 52, to enclose test strip 28 therein. Blister package 56 includes an elongated cavity to hold strip 28 and an expansion cavity-housing 58 at the one end to form a generally toothbrush-shaped cavity within plastic blister package 56 and strip 52. Selected test strip 28 is sealed and enclosed within blister package 56.

FIG. 8 shows a side sectional view of the blister-package test device 50 prior to use. FIG. 9 shows blister-package test device 50 with one end peeled back by peel tab 54, to expose expansion housing cavity 58 and sponge 32 of test strip 28, so that a defined amount of a liquid sample can be added, for example, by pipet, as shown. In a preferred embodiment, cavity 18 is triangular-shaped similar to sponge 32 as shown in FIG. 9.

FIG. 10 illustrates test device 50 after addition of the liquid sample, and with peel tab 54 resealed and with sponge 32 fully expanded by the liquid sample within housing cavity 58 and ready to incubate.

FIG. 11 illustrates test device 50 upside down and placed in one of two cavities 47 in incubator 46. FIG. 12 illustrates the technique of adding the liquid sample with a pipet, while peel tab 54 is pulled away from the end of test device 50 in incubator 46. Test device 50 is sealed and incubated. The test results of the completed test can then be read through a transparent top cover of blister package 56, as shown in FIG. 13, to provide positive or negative test results.

Inhibition assay test strip 28 (FIG. 7) selected for beta-lactams in milk is a quick test for beta-lactams in commingled raw and pasteurized milk. In operation, temperature gauge 48 in incubator 46 is checked to ensure an incubator temperature of about 55° C. For example, temperature indicator 48 may be colored, for example, green, for use. Test device 50 is placed in one cavity 47 of incubator 46 with the flat side facing up and peel tab 54 peeled back enough to expose sponge 32, for example one centimeter. The milk is mixed thoroughly before testing, and about 0.2–0.7 ml, preferably 0.3–0.5 ml, is added by pipet to exposed sponge 32. Adhesive tape tab 54 is resealed by hand pressure and incubator 46 cover is closed. Test device 50 is incubated, for example, at least 6 to 8 minutes and then removed from incubator 46 and held vertically and a comparison made within about one hour between test zone 38 and control zone 40. If no control zone 40 appears, the test is invalid. A negative test occurs when reference zone 38 is the same or darker than control zone 40. A positive test is indicated when test zone 38 is absent or clearly lighter than control zone 40.

In more detail, test device 10 capable of detecting analytes in biological fluids includes the following components:

Sponge 32, a compressed material, such as cellulose, is capable of absorbing a biological fluid and acting as a prefilter to remove coarse contaminants, such as hair, dirt, etc. Sponge 32 is sized to absorb a fixed amount of sample required to complete the assay. This compressed material, when expanded and contacting the inside wall of housing 12, causes sufficient pressure to drive capillary flow along the components sponge 32, mobile-phase support 33, stationary-phase membrane 36, and disposal zone 43 and in the time required (about 3 to 8 minutes) for a commercially marketable test. Sponge 32 overlaps mobile-phase support (conjugate pad) 33 by 1 to 10 mm such that, when an aqueous sample, such as milk, is added to sponge 32, the sample flows onto mobile-phase support 33.

The test device can use a biological receptor that is tagged with ample amounts of color, infrared, fluorescent or luminescent dyes. The liquified sample (e.g. milk, corn, feed, peanut extract, meat extract, serum, environmental sample, etc.) resuspends the tagged-receptor which is previously stabilized with readily soluble additives in a mobile-phase composition. The time controlled released tagged-receptor reacts with the analyte in the sample while moving into a reaction zone on stationary-phase membrane 36.

Residue specific monoclonal antibodies are also included in the mobile-phase composition to specifically bind excess residue with high sensitivity, thus, adjusting the sensitivity for those specific residues downward (to make the test less sensitive). As less of these residues are available to compete with the broad spectrum receptor, the sensitivity is adjusted closer to regulatory requirement. For example, initial sensitivity of beta-lactam receptor to cephapirin is 3–5 ppb. Including specific antibodies to cephapirin the sensitivity is adjusted to 15–20 ppb. Food and Drug Administration regulatory "safe" level in raw, commingled milk is 20 ppb.

Housing 12 should be used to allow for addition of biological sample, either by dipping, pouring or pipetting. Housing 12 can be constructed of a flexible or hard material, such a polystyrene, polypropylene, or polyethylene.

Mobile-phase support 33 can be made of a glass membrane or a polymer, such as polyester or polyethylene, that acts as a secondary filter for removal of less coarse materials (somatic cells). The support is pretreated with a chemical solution, such as 0.01 to 0.2 M sodium citrate pH 6–8, capable of neutralizing interferences found in biological samples. The mobile-phase support overlaps stationary-phase membrane 36 (reaction strip) by about 1 to 4 mm.

The color or fluorescent receptor/antibody coated microspheres are suspended in a solution containing protein e.g. albumin bovine (BSA), glycerol, sugar or equivalent thereof e.g. sucrose (SUC) or trehalose (TRE), polyethylene glycol 8,000 MW (PEG), amino acid mixtures (AA) or detergents as stabilizers and wetting agents, and absorbed or sprayed in the membrane using a spraying instrument such as is available from Biodot. Furthermore, the residue specific antibodies are spray dried or immobilized in this matrix. Sample buffering is also optimized here using a buffer with a given pH, salt or any required cofactor needed to optimize the receptor/antibody binding kinetic.

A mobile-phase includes highly specific binding proteins, such as an enzyme, or monoclonal antibodies capable of binding to an analyte and titrated to a known concentration to make unavailable for further reaction/detection of a known amount of analyte. This unavailability for further reaction/detection allows for the adjustment of a detection level of one or more analytes to a specified level of concern. For example, in ceftiofur, a beta-lactam with a tolerance level of 50 ppb in milk, sensitivity can be changed from 5 ppb to between 40–50 ppb by the addition of a monoclonal antibody specific for ceftiofur. The specific monoclonal antibody competes with the labeled receptor to remove a specific analyte from binding to a receptor or antibody which is capable of binding to a family of related compounds.

Highly purified proteins, such as, beta-lactam receptor or anti-tet IgG, prepared by affinity purification and/or a combination of hydrophobic/ion-exchange chromatography, are attached to a colored, fluorescent, or infrared probe which can be observed by optical/instrumental means or both. Attachment of proteins to a probe is called binding protein/probe complex.

Mobile-phase composition 34, such as gold beads, is made to a particle size between 10 and 60 nm, preferably 30–40 nm. To form the beads, 1 ml of a filtered 40 mg/ml gold chloride solution is added to 360 ml of boiling water into a clean one liter flask. To 35 ml of water is added 4 ml of 1% sodium citrate solution. The citrate solution is added to the gold solution while boiling. After refluxing for 20 to 30 minutes the bead solution is cooled and brought to pH of 7.3 with potassium carbonate.

In a specific embodiment, the receptor (960 units) in 5–20 ml of 2 mM potassium phosphate is diluted in water to 75 ml and added to the gold bead solution while mixing. This solution is incubated at 37° C. for at least one hour and generally overnight. After incubation 10% BSA (bovine serum albumin) solution is added to bring final BSA concentration to 0.2% and solution is incubated an additional 30 minutes. This bead solution is centrifuged at 8,000xg for 45 min. The bead pellet is washed and centrifuged 2 times with 10 mM potassium phosphate buffer, pH 7.2, containing 0.2% BSA and 0.05 surfactant, such as tween 20 or Bioterge AS-90 (sodium olefin sulfonate).

The beads are then resuspended in 10 mM Potassium phosphate, pH 7.2, containing 0.2% BSA, 50 mM sodium chloride, 0.05% of surfactant and preservative. Glycerol is added to the beads to give a 16.7% concentration.

Specific beta-lactam antibodies, for example, are added to the beads to target detection levels for individual beta-lactam drugs at the established safe level. Cephapirin antibody is diluted with spray solution and added to the beads to give a final concentration at about 8%. Ampicillin antibody is diluted 1 part to 9 parts with spray solution and added for a final concentration of approximately 2.85%. Ceftiofur antibody is diluted with spray solution and added to beads to a final concentration of 40% of antibody and spray solution. Two spray solutions have been used. One consists of 10 grams BSA, 2 grams saccharin, 0.05% surfactant and preservative in 10 mM sodium phosphate buffer at pH 7.4. The other consists of 10 grams BSA, 40 grams sucrose, 0.05% surfactant and preservative in 10 mM phosphate buffer at pH 7.4. For spraying, the bead solution is diluted with spray solution, usually 6 parts beads to 4 parts spray solution.

The beads can be sprayed into a mobile-phase support 33, such as a pretreated Porex® pad (treated with sodium citrate and SDS). Porex® Lateral-Flo™ Media is a rigid pore structure made from high density polyethylene from Porex Technologies. The mobile-phase composition is diluted, for example, with 10 mM sodium phosphate buffer, pH 6.9, and sucrose to give a sucrose concentration of 4%. The mobile-phase composition is sprayed on the nitrocellulose or other suitable substrate at 0.6 $\mu$l to 1.5 $\mu$l/cm. The control zone, containing antibody to the receptor, is sprayed at the same time and the nitrocellulose is dried to 55° C. for 1 hour. Zone thickness is adjusted by added BSA to mobile-phase composition. The mobile-phase composition is sprayed, using a machine manufactured by Ivek, Biodot, or Camag. The mobile-phase composition is sprayed on the upper portion of the mobile-phase support 33, such that mobile-phase composition 34 does not overlap sponge 32, but rather mobile-phase support 33 overlaps sponge 32 by placing the topmost portion of sponge 32 about 1 to 7 mm before the sprayed portion of mobile phase. The mobile-phase support is dried for one hour at 55° C. and tested in an assay system for sensitivity of all the drugs. Antibody concentrations in the mobile-phase composition solution are then adjusted as needed.

For the mobile phase to obtain the best color or fluorescence response, highly purified proteins (beta-lactam receptor or anti-tet IgG for example) can be prepared by (I) affinity purification and/or (ii) a combination of hydrophobic / ion exchange chromatography. For beta-lactam receptor for instance, the target is 50–500 units per mg protein (1 unit is equivalent to binding of 1 ng penicillin G).

For color, infrared, or fluorescent probes, the receptor/antibody can be either a color, infrared, or fluorescent dye immobilized in, for example, a 0.02–10 micrometer microsphere or colloidal gold. These supports either absorb protein or exhibit functional groups such as $NH_2$, COOH or CHO for covalent protein binding. The microsphere generally is coated with high concentration of highly specific binding proteins.

Typically, the stationary-phase membrane is formed of nitrocellulose, nylon, polyethylene or another suitable material. In the stationary phase, the analyte representative drug is attached with high specific ratio to a carrier e.g. a protein such as BSA, IgG or Protein A. It is generally desirable in the stationary phase to create a molecular sieve that efficiently captures the tagged-receptor/antibody. Stationary-phase membrane 36 has multiple reaction zones present and includes test zone 38 sprayed in a line using a suitable spraying instrument. The purpose of the test zone is to capture unreacted binding protein/probe complex for viewing or measurement. Test zone 38 (FIG. 6) consists of an analyte of detection; that is, ceforanide or a member of the analyte family, that is, beta-lactams, coupled to a carrier protein, that is BSA, IgG, KLH, suspended in a 5 to 100 mM buffer solution (such as phosphate or buffer base) at a pH range of 3–10, preferably 6–8. Total protein concentration of the antibody solution ranges from 0.2 to 100 mg/ml. The analyte-carrier, dissolved in a buffer solution e.g. 10 mM phosphate buffer, pH 6.9 containing sugar, such as trehelose or other additives, is sprayed as a line on the stationary-phase membrane. Tentacle immobilization of analyte conjugate to a multiple binding site carrier, such as Protein A or latex microspheres, increases stability and binding capacity. Subsequent heat treatment of the membrane further stabilizes the adhesion. On the test device, a second test zone can be added to the reaction zone to test for a second analyte. For example, the first test zone can have a first binder for amoxicillin, ampicillin, ceftiofur, cephaparin and penicillin G. The second test zone can have a second binder for cloxacillin. Alternatively, the first test zone can test for beta-lactams and the second test zone can test for sulfonamides. Additional test zones can be added to test for additional analytes.

The reaction zone also includes control zone 40, shown in FIG. 13, sprayed in a line form using a suitable spraying instrument. A purpose of control zone 40 is to capture binding protein/probe complex that has not bound to test zone 38. Control zone 40 can consist of an antibody specific to the binding protein/probe suspended in 5 to 100 mM of a buffer solution (phosphate or Trizma) in a pH range of 3 to 10. Total protein concentration of antibody solution ranges generally from 0.2 to 100 mg/ml.

In one embodiment, the material for ceforanide-SM is added to the SMCC-BSA-NEM solution and the reaction continues with stirring overnight at 4° C. The ceforanide-BSA is dialyzed to remove free ceforanide. Control zone includes an antibody to the tagged receptor or broad spectrum antibody that is immobilized as a line parallel to the test zone. Thus, mobile-phase composition receptor/antibody captures in this line regardless of presence or lack or analyte in the sample. The control zone consists of an antibody made to the beta-lactam receptor. The receptor is purified by affinity chromatography. The antibody to the receptor is diluted in 10mM sodium phosphate buffer and sprayed at 0.6μl/cm to 1.5μ/cm. Zone thickness is adjusted by adding BSA to the receptor antibody solution.

A comparison of the control zone to the test zone yields the test result. Typically, if the control zone is darker than the test zone, analyte is present at detection level or greater (see FIG. 6).

Disposal zone 43, shown in FIG. 7, typically is made of pressed cellulose or other absorbent material to keep the sample flow consistent and to retain the reacted sample. The disposal zone generally overlaps the stationary-phase membrane 36 by about 1 to 5 mm.

The mobility of the sample (milk, blood serum or other fluids) is tested to optimize reaction times and uniformity. High pore size membranes (15 to 140 μm) are used to allow flow of viscous samples like milk or serum.

The disposal zone 43 typically includes an absorbent pad that is an absorbing membrane made of a cellulose, synthetic sponge or other material. This pad keeps the sample flowing and stops flow at saturation, thus giving the assay time control and reducing background noise.

In another specific embodiment, an aqueous biological sample is added to sponge 32 of the test device. Sponge 32 serves as a sample pad which expands as it absorbs the sample. Sponge pad 32 overlaps mobile-phase support 33, and the fluid flows onto the mobile-phase support 33 where the mobile-phase materials dissolve into the biological fluid. Analytes present in the sample begin binding with the specific binding protein(s) attached to the probe. At the same time, specific bound or unbound antibodies or binding proteins bind with specific analytes to adjust their sensitivity to the test. Mobile-phase support 33 overlaps stationary-phase membrane 36, and the biological fluid, along with mobile-phase composition 34 (colored beads), continue to react as materials flow up stationary-phase membrane 36. When the binding protein/probe complex reaches test zone 38, a portion of the binding protein/probe complex binds to the test zone. In a positive sample, analyte in the sample is bound to the binding protein/probe complex, reducing the amount of binding protein/probe complex capable of binding to the test zone 38. When the material reaches control zone 40, a portion of binding protein/probe complex binds control zone 40. Excess reagent is then absorbed into disposal pad 43.

In a negative sample, reagents are titrated so that test zone 38 has the same or preferably a greater amount of the probe binding to it than in control zone 40. Conversely, in a positive sample, control zone 40 has a greater amount of the probe binding to it than test zone 38.

In still another embodiment, a beta-lactam test is made to assay for beta-lactams in milk at a safe level. A partially purified beta-lactam receptor from BST (*Bacillus stearothermophilus*) is bound to a colloidal gold solution to make a beta-lactam binding protein/gold bead probe. This is sprayed on the mobile-phase support 33 along with monoclonal antibodies to ceftiofur, cephapirin, ampicillin and amoxicillin to reduce the sensitivity of these four antibiotics so that the test gives a desired dose response. On test zone 38 is sprayed a ceforanide-BSA conjugate, and to control zone 40 is sprayed an antibody to the BST beta-lactam receptor. A raw-milk sample, between 0.1–1.0 ml preferably, is applied to the sample pad by pipette, and the test strip is incubated at 55° C. After about eight minutes, test strip 10 is removed from the incubator and analyzed. If test zone 38 is darker or the same color as control zone 40 line, the sample is negative, and, if test zone 38 is lighter than control zone 40, the sample is positive.

Test results are shown in Table 1 as follows:

TABLE 1

Beta-lactam assay in milk using lateral flow test device.

| Number of Assays | Sample | Result |
| --- | --- | --- |
| 30 | zero control | all negative |
| 10 | penicillin G at 5 ppb | all positive |
| 10 | penicillin G at 4 ppb | 5 positive, 5 negative |
| 10 | penicillin G at 3 ppb | 3 positive, 7 negative |
| 10 | ampicillin at 6 ppb | all positive |
| 10 | ampicillin at 4 ppb | all positive |
| 10 | ampicillin at 3 ppb | 5 positive, 5 negative |
| 10 | amoxicillin at 6 ppb | all positive |
| 10 | amoxicillin at 4 ppb | 8 positive, 2 negative |

TABLE 1-continued

Beta-lactam assay in milk using lateral flow test device.

| Number of Assays | Sample | Result |
|---|---|---|
| 10 | amoxicillin at 3 ppb | 4 positive, 6 negative |
| 10 | ceftiofur at 30 ppb | 3 positive, 7 negative |
| 10 | ceftiofur at 40 ppb | 8 positive, 2 negative |
| 10 | ceftiofur at 50 ppb | 10 positive |
| 10 | cephapirin at 12 ppb | 2 positive, 8 negative |
| 10 | cephapirin at 15 ppb | 5 positive, 5 negative |
| 10 | cephapirin at 20 ppb | 10 positive, 0 negative |

The described test is an inhibition-type assay. Analyte in the sample binds with a beta-lactam binding protein/mobile-phase composition probe and inhibits binding to a stationary beta-lactam bound to the surface of the membrane. Addition of a specific monoclonal antibody to ceftiofur has altered its inhibition level from approximately five ppb to between 40 and 50 ppb. Addition of a specific monoclonal antibody to cephapirin has reduced its sensitivity from approximately 3–5 ppb to between 15 to 20 ppb.

The test device of the invention can be used with test strips for detecting a variety of analytes, such as toxins like alfatoxins, pesticides such as organophosphates and carbamates; as well as beta-lactams, such as penicillin, ampicillin, amoxicillin, cloxacillin, dicloxacillin, oxacillin, ceftiofur, and cephapirin; tetracyclines, such as chlortetracycline, oxytetracycline and tetracycline; sulfonamides, such as sulfamethazine, sulfadimethoxine, sulfamerazine, sulfathiazole and sulfadiazine; macrolides, such as erythromycin, spiramycin and tylosin; aminoglycosides, such as gentamicin, neomycin and DH/striptomycin; and others such as dapsone, chloramphenicol, novobiocin, spectinomicin and trimethoprim, to detect the maximum residue-analyte limits in the sample. Most of the elements for each test are the same except the chemistries of the mobile phase, test zone and control zone, which are tailored to the specific analyte detection.

As the sample flows from stationary-phase membrane 36 into disposal zone 43 (until absorbent pad saturation), the unreacted tagged-receptor is captured in the reaction zone by an immobilized group representative analyte. Chemical residue in the sample reacts with the tagged-receptor making it unreactive to the test line. Thus, the more residue in the sample, less signal is detected in the test zone.

Stationary-phase membrane is constructed from highly porous matrix suitable for viscous samples, such as milk or meat extracts. In each zone, a combination of soluble polymers is embedded (e.g. proteins, polyethylene glycol, etc.) to control the kinetics of mobility of the sample from the mobile-phase composition to the reaction zone and in the reaction zone itself.

Data were generated with microbial beta-lactam receptor, specific antibodies for sulfamethazine, tretracycline and aflatoxin (pt CHII AOAC) to detect for the presence of corresponding residues in milk or other matrices such as serum. Levels of 3–5 ppb penicillin G (PEN G) and 5–20 ppb cephapirin, 30–100 ppb oxytetracycline (OXT), 10–100 ppb sulfamethazine (SMZ) and 2–40 ppb aflatoxin B1 were detected with these experiments.

An incubator with adjustable temperature ranging up to 70° C. generally is preferred. The test device can employ a portable colorimeter, or refractive fluorometer, or infrared reader. In a preferred embodiment, the test device includes a reader that is used to read a test strip that contains two lines. The control line is a reference line that insures that the test has been run correctly. The control line is also used as a reference when the reader determines if the sample is positive or negative. The test line indicates the concentration of the substance being tested. The darker the test line the higher the concentration of the substance in the sample. The reader includes two components, a controller and a meter.

The meter reads the strip when the strip is inserted into the meter and the meter is given the command to read the strip. The meter then strobes a series of light emitting diodes (LED), preferably, seven. The light emitted from the LED's is bounced off the strip being read. The light is then reflected onto a 128×1 Opto Sensor. The sensor sends 128 date values representing the intensity of the light at each of the 128 pixels to an on board microcontroller. The pixel date is stored in the meter's memory. The dark areas of the strip have a lower value than do the light areas. This information is later used to calculate the intensity of the two lines being read.

The controller sends a command to the meter to request the date read by the meter. The controller performs calculations on the date to determine the intensity of the two lines. If the test line is darker than the control line then the test is said to have a negative result. If the test line is lighter than the control line then the test is said to have a positive result. The controller displays to the user the result as well as a raw value representing the difference in the intensity of the two lines.

Integration of incubator with fiber optics to read the results can provide the test with full automation.

The test unit, such as in blister pack form, is placed in an incubator which is heated to about 56.5° C.±1° C. The tape is peeled back and a liquid sample, 0.3 ml, is added to the sample well and the tape is resealed. The test unit is incubated for at least five minutes.

Once the sample is added to the sample well, it is absorbed by the sample sponge which expands inside the well. The top portion of the plastic well prevents the sponge from expanding fully. The pressure of the sponge against the well on the top and the mobile-phase support on the bottom gives some added force to propel the liquid sample up the test strip at a faster rate than would otherwise occur. The sponge expands and the sample next moves onto the mobile-phase support and interacts with the mobile-phase composition. The mobile-phase composition starts to move onto the nitrocellulose. During this time incurred residues or analytes in the sample bind to the receptor or antibody attached to the mobile-phase conjugate.

When the mobile-phase composition reaches the test zone, the free labeled receptor binds to the test zone resulting in a dark bottom line. Receptor or antibody with bound analyte does not bind to the test line resulting in a noncolored or light colored test zone line. This is a sequential inhibition-type assay where the compound of concern does not bind to the test zone. The mobile-phase composition moves past the control zone and onto an absorbent pad which serves as a reservoir to catch unbound mobile-phase composition.

FIGS. 14–17 illustrate an embodiment of the device 101 in transparent blister package 103 which includes transparent-tape plastic seal strip 111, to enclose test strip 105 therein. Blister package 103 includes an elongated cavity to hold strip 105 and expansion cavity-housing 104 to form a generally tooth-brush shaped cavity within plastic blister package 103 and strip 105. As shown, expansion cavity-housing 104 is triangularly shaped. The blister package 103 includes one movement restriction zone 114 surrounding the disposal pad 106 and another movement restriction zone 115 surrounding adhesive backing 113 at the point at which backing 113 protrudes before sample absorbing sponge 109. Movement restriction zones 114, 115 form pinch points which secure strip 105 within blister package 103. The device, therefore, is designed so that one location at which narrowing occurs is at disposal pad 106 in which zone there is located an absorbent material which acts as an absorbent pad. Preferably, the device is designed, and placement of components located so that, approximately one cm of adhesive backing protrudes before the sample sponge pad contained within the sample application zone. The strip is, therefore, secured in place at either one or both ends, thereby allowing unimpeded sample flow.

Figure 17:
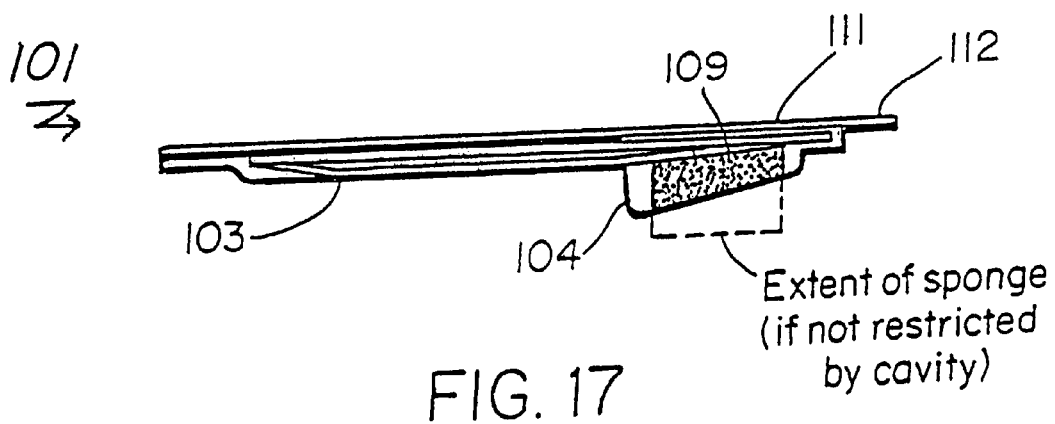

FIG. 15 shows a side sectional view of blister-package test device 101 prior to use. FIG. 15 shows blister-package test device 101 with one end peeled back by peel tab 112, to expose expansion housing cavity 104 and dry filter-absorbent sponge pad 109 of test strip 105, so that a defined amount of a liquid sample can be added, for example, by pipette, as shown. FIG. 17 illustrates test device 101 after addition of the liquid sample, and with peel tab 112 resealed and with the sponge pad 109 fully expanded by the liquid sample within housing cavity 104 and ready to incubate.

FIG. 18 is an enlarged view of absorbent pad 109 of the test device. FIG. 18 illustrates the narrowing of the inner walls of the housing in zone A to form movement restriction zone 114 securing the adhesive backing 113 and thereby strip 105 (not shown in FIG. 18) is held in place within the plastic blister 113. FIG. 18 also illustrates the air space zone B existing between strip 105 and adhesive backing 113 which allows consistent flow of sample along the strip.

The invention will now be described by the following examples:

EXAMPLE #1
Lateral Flow Test Kit for Tetracyclines in milk, serum and meat extract A lateral flow test kit for tetracyclines includes: a test zone made of BSA-TET conjugate, a control line made of Goat Anti-Rabbit IgG, and a mobile phase made of Anti-TET Rabbit Antibodies—Gold conjugate BSA-TET Preparation 444.4 mg of tetracycline is dissolved in 5 ml of THF and 1.5 ml of 0.2 M Sodium Bicarbonate is slowly added. 240.3 mg of L-Cystine are added together with 111µl of formaldehyde 37%. The mixture is incubated at 40° C. for 30 minutes and placed on a shaker at room temperature for 2 hours. The mixture is centrifuged at 4,000 rpm for 3 minutes. A minimum yield of 60% product is verified by HPLC. 463 mg of DL-Dithiothreitol is then added to the supernatant. The mixture is placed on a shaker at room temperature for 30 minutes and centrifuged at 4,000 rpm for 3 minutes. The supernatant is precipitated into acetone and the TET-CYS precipitate collected, washed and dried under nitrogen. 1.0 g of protease-free BSA is dissolved in 8 ml of 50 mM Sodium Phosphate pH 7.2. Twenty mg of N-Methylmaleimide is added and the mixture is placed on a shaker at room temperature for 2 hours. The mixture is dialyzed at 4° C. against 10 mM Sodium Phosphate pH 7.2. Fifty mg of Sulfo-SMCC is added to a volume of NEM-BSA containing 365 mg of protein. The mixture is place on a shaker at room temperature for 2 hours. The mixture is dialyzed at 4° C. against 50 mM sodium Phosphate pH 7.1 (2 L×4 hours×4 changes). TET-CYS is dissolved in a volume of NEM-BSA-SMCC containing 150 mg of protein. Sufficient 50 mM sodium Phosphate pH 7.1 buffer is added to the combined solution to get a protein concentration of 50 mg/ml. The tube is placed on a shaker at room temperature for 2 hours. BSA-TET mixture is purified with 5 mM Sodium Phosphate pH 6.8 using a 10DG desalting column from Bio-Rad (cut-off at 6,000 daltons). All the protein containing fractions are combined and tested for protein (using Bio-Rad Standard Protein Assay) and tetracycline activity (using a Charm-II tetracycline assay). A minimum of 2 units/µg is required. BSA-TET is kept at a temperature of −20° C.

Affinity Purification of Anti-Tet IgG CLT-COOH Preparation 239 mg of Chlortetracycline HCL are dissolved in a mixture of 1.5 ml of DMF and 4 ml of 0.2 M Sodium Bicarbonate. 130 mg of 6-Aminocaproic Acid and 105 µl of formaldehyde 37% are added. After vortex, the mixture is incubated at 40° C. for one hour and placed at room temperature on a shaker for one hour and precipitated from acetone. This precipitate is collected and dried under nitrogen.

Gel preparation

Sepharose EAH (from Pharmacia Biotech) are washed with 10 ml of 0.5 M NaCl pH 6.0 and is suspended in a solution of 50 mg of CLT-COOH in 2 ml of 0.5 M NaCl pH 6.0. The pH is adjusted between 4.5 and 6 and 200 µl of a solution containing 100 mg of EDC in 1 ml of 0.5 M NaCl pH 6.0 is added. The pH is readjusted to 4.5–6 and the mixture is placed on a shaker at room temperature for 20 minutes. The EDC addition is repeated two more times. The gel is poured into a suitable column and the output is collected in a test tube. The column is washed alternately using 4 ml aliquots of Binding Buffer (0.1 M Trisma 0.5 M NaCl pH 8.5) and Washing Buffer (0.1 M Sodium Acetate 0.5 M NaCl pH 4.0). The last wash is performed using Binding Buffer and is continued until the output pH is 8.5.

Antibodies Purification

The column is loaded with a mixture of 30 ml of rabbit anti-TET serum in 30 ml of Binding Buffer. After loading, the column is washed with Binding Buffer until no protein leaks. Anti-TET specific antibodies are eluted using 1 ml aliquots of Elution Buffer (from Pierce) and collected in test tubes containing 200 µl of 1.0 M Sodium Phosphate pH 9.4. The elution is continued until no protein leaks. The high protein containing tubes are tested for protein using Bio-Rad Standard Protein Assay. 12 µ(microliters) of a 10% BSA solution are added to each tube.

The fractions are dialyzed against 20 mM sodium phosphate and tested for specific activity using either a lateral flow test or a Charm-II tetracycline assay. An activity greater than 100 units/mg is required.

Gold Preparation 200 ml of HPLC water are boiled in a 500 ml Erlenmeyer rapped in aluminum foil. 4 ml of 1% Gold Chloride are added to the boiling water and the solution is mixed for 3 minutes. 12 ml of 1% Trisodium Citrate are added to the boiling solution. Vigorous mixing is continued for an additional 3 minutes. The flask is removed from the hot plate and allowed to cool to room temperature.

Gold-Antibodies Conjugation

Ten ml of 20 mM Borate is added to 100 ml of gold. 2.5 ml of an appropriate dilution of affinity purified antibodies in 20 mM Sodium Phosphate 0.15 M NaCl pH 7.3 are slowly added. The solution is thoroughly mixed for 30 minutes at room temperature. 10 ml of a solution containing 10% of BSA in 2 mM Borate is added and the mixing is continued for 30 minutes. The solution is dispensed in 4×50 ml centrifuge tubes and centrifuged at 15,000 rpm for 1 hour at 10° C. The supernatant is discarded and the pellet is resuspended in a solution containing 0.1% BSA in 2 mM Borate. The solution is centrifuged again and the pellet resuspended to a final absorbance of 30 at 520 um. 20 % of glycerol and 0.05%NaN$_3$ are added and the solution kept at −20° C.

Test Zone (BSA-TET)

BSA-TET conjugate is sprayed in the nitrocellulose at a concentration of 5 mg/ml in a 5 mM Sodium Phosphate pH 6.8 solution containing 10 mM dipotassium oxalate, 4% sucrose and 0.6% BSA. The volume sprayed is about 0.6 to 1.0 μl/cm.

Control Zone: Goat Anti-Rabbit IgG

The solution for the control zone consists of a mixture of 2–10% Goat Anti-Rabbit IgG (from Sigma) in a 5 mM Phosphate pH 6.8 buffer containing 30 mg/ml BSA. The volume sprayed in the nitrocellulose is 1.5 μl/cm.

Mobile Phase (Anti-TET IgG—Gold Conjugate)

Anti-TET Antibodies—Gold conjugate is sprayed in the treated mobile-phase support in a solution containing 60% of gold conjugate/Glycerol and 40% of diluent (10% BSA and 40% sucrose in 10 mM Sodium Phosphate pH 7.4). The volume sprayed is 2–5 μl/cm.

TABLE 2

Test Performance: Dose Response Curve for M.R.L.-TET (n = 6)
Level for multiresidue limit.: Oxytetracycline (OXT) 100 ppb
Chlortetracycline (CLT) 100 ppb
Tetracycline (TET) 100 ppb

| Drug (in ppb) | % Negative | % Positive |
| --- | --- | --- |
| Negative | 100 | 0 |
| OXT 100 | 0 | 100 |
| OXT 60 | 33 | 66 |
| OXT 30 | 50 | 50 |
| OXT 10 | 83 | 17 |
| CLT 100 | 0 | 100 |
| CLT 60 | 50 | 50 |
| CLT 30 | 66 | 33 |
| CLT 10 | 83 | 17 |
| TET 100 | 0 | 100 |
| TET 60 | 0 | 100 |
| TET 30 | 0 | 100 |
| TET 10 | 83 | 17 |
| TET 5 | 100 | 0 |

EXAMPLE 2

Lateral Flow Test Kit for Quinolone in Milk, Meat or Serum

The lateral flow test kit for quinolone includes: a test zone made of BSA-quinolone conjugate, a control zone made of Goat Anti-Rabbit IgG, and a mobile phase made of Anti-quinolone antibodies—Gold conjugate.

Test Zone: BSA-QUINOLONE Conjugate Formation

Quinolone BSA Preparation.

Specific Conjugate (or Immunogen).

The following conjugation linking the carboxylic acid of quinolones to the primary amine group on proteins. For Immunogen a KLH or OVA can be used while for the assay BSA is used. 40 mg. Ciprofloxacin or enrofloxacin are dissolved in water or DMSO respectively, and then added drop wise to a stirred BSA solution (100 mg/10 ml 0.1M MES buffer, pH 4.7). 100 mg of 1-ethyl-3[-dimethylaminopropyl] carbodiimide hydrochloride (EDC) are added and solution is stirred for 2 hours at RT in the dark. The product is then dialyzed 3 times against 1000 ml of 20 mM phosphate buffer pH 7.2, 150 mM NaCl. Unreacted quinolone can be monitored by TLC using Silica Gel F and methylene chloride: methanol: acetic acid (15:5:0.1). BSA-quinolone conjugate can be visualized at the start line while unreacted quinolone moves to about Rfof0.4.

Broad Spectrum Conjugate

In this embodiment, the quinolones are linked through the secondary amine on the pyprazyl moiety to a free sulfydryl group on the protein. Sulfosuccinimidyl 4-[N-maleimidomethyl]-cyclohexane-1carboxylate (Sulfo-SMCC) is used for this reaction. BSA (100 mg) is first treated with 5 molar excess of Traut's reagent (2-iminothiolane*HCl) to convert primary amines to sulfydryl group at pH 7–10. After dialysis the modified BSA is combined with ciprofloxacin (50 mg) and Sulfo-SMCC (20mg), mixed on shaker at RT for 2 hours. The BSA-N-ciprofloxacin is dialyzed at 4° C. against 50 mM Sodium Phosphate pH 7.1 (2L×4 hours×4 changes). The protein concentration is adjusted to 20mg/ml BSA with ultrafilter using Bio-Rad Standard Protein Assay. Conjugate is kept at a temperature of−20° C.

Test Zone Formation

BSA-QUINOLONE conjugate is sprayed in the nitrocellulose at a concentration of 5–20 mg/ml protein in 1–3% BSA or/and 1–4% sucrose. The volume sprayed is 1–1.5 μl/cm.

Control Zone: Goat Anti-Rabbit IgG

The solution is prepared the same as described above in the tetracyclines example.

Mobile Phase: Rabbit Anti-QUINOLONE Antibodies—Gold Conjugate

Antibodies Affinity Purification.

Gel Preparation.

For preparation of ciprofloxacin/enrofloxacin specific antibodies, 3 ml of 4B Sepharose EAH (from Pharmacia Biotech) are suspended in 10 ml of 0.5 M NaCl pH 6.0. After vortex, the mixture is centrifuged at 3,400 rpm for 5 minutes and the supernatant discarded. The wash is repeated 4 times. 3 g of the gel washed is suspended in a solution containing 100 mg of EDC in 1 ml of DMSO is added the mixture is placed on a shaker at room temperature for 20 minutes. The EDC addition is repeated two more times.

The gel is poured into a suitable column and the output is collected in a test tube. The column is washed alternately using 4 ml aliquots of Binding Buffer (0.1 M Trisma 0.5 M NaCl pH 8.5) and Washing Buffer (0.1 M Sodium Acetate 0.5 M NaCl pH 4). Each wash is eluted into a clean test tube. The fluorescence of the output at 366 nm is monitored and the washings continued until no fluorescence is visible. The last wash is performed using Binding Buffer and is continued until the output pH is 8.5.

Antibodies Purification

The column is loaded with a mixture of 30 ml of rabbit anti-enrofloxacin serum in 30 ml of Binding Buffer. After loading, the column is washed with Binding Buffer until no protein leaks. Anti-quinolone specific antibodies are eluted using 1 ml aliquots of Elution buffer (from Pierce) and collected in test tubes containing 200 μl of 1.0 M Sodium phosphate tubes are tested for protein using Bio-Rad Standard Protein Assay. 12μl of a 10% BSA solution are added to each tube.

The fractions are tested for specific activity using a lateral flow test strip assay with 40 nm gold beads. The antibodies are dialyzed against 20 mM phosphate buffer, 150 mM NaCl and kept at −20° C.

For preparation of broad spectrum antibodies, 100 mg of sarafloxacin are dissolved in a 5 ml DMSO and pass through Pharmacia HiTrap NHS activated cartridge. After 1 hour excess sarafloxacin is washed with DMSO followed by 50 mM phosphate buffer pH 7.2.

The column is washed alternately using 4 ml aliquots of Binding Buffer (0.1 M Trisma 0.5 M NaCl pH 8.5) and Washing Buffer (0.1 M sodium Acetate 0.5 M NaCl pH 4.0). Each wash is eluted into a clean test tube. The color of the output is monitored and the washings continued until no color leaks. The last wash is performed using Binding Buffer and is continued until the output pH is 8.5.

Antibodies Purification

The column is loaded with a mixture of 30 ml of rabbit anti-enrofloxacin serum in 30 ml of Binding Buffer. After loading, the column is washed with Binding Buffer until no protein leaks. Anti-quinolone specific antibodies are eluted using 1 ml aliquots of Elution Buffer (from Pierce) and collected in test tubes containing 200µl of 1.0 M sodium Phosphate pH 9.4. The elution is continued until no protein leaks. The high protein containing tubes are tested for protein using Bio-Rad Standard Protein Assay. 12 µl of a 10% BSA solution are added to each tube.

The fractions are tested for specific activity using either a lateral flow test of a tetracycline assay. An activity of greater than 100 units/mg is preferred. The antibodies are kept at a temperature of −20° C. The column is regenerated by washing alternately with 4 ml of Pierce Elution Buffer and 4 ml of Binding Buffer (3 cycles).

Gold Bead Preparation

Gold bead preparation is conducted by the same method as described above in the tetracyclines example.

Gold-Antibodies Conjugation

Gold-Antibodies conjugation is conducted the same method as described above in the tetracyclines example.

Spraying

Antibodies-Gold conjugate is sprayed in the treated mobile-phase support in a solution containing gold conjugate in final 5% BSA and 20% sucrose. The volume sprayed is 2–10 microliter per cm.

TABLE 3

Test Performance: Dose Response Curve for Quinolones
Target levels for multiresidue limit are in milk: Ciprofloxacin and enrofloxacin 10 ppb in meat:
Ciprofloxacin and enrofloxacin 30 ppb

| Toxin levels (in ppb) | Estimated % Negative | Estimated % Positive |
|---|---|---|
| Negative - Milk | 100 | 0 |
| Enrofloxacin 30 | 0 | 100 |
| Enrofloxacin 10 | 0 | 100 |
| Enrofloxacin 5.0 | 10 | 90 |
| Enrofloxacin 2.5 | 75 | 25 |
| Enrofloxacine 1.0 | 100 | 0 |
| Ciprofloxacin 30 | 0 | 100 |
| Ciprofloxacin 10 | 0 | 100 |
| Ciprofloxacin 5.0 | 10 | 90 |
| Ciprofloxacin 2.5 | 75 | 25 |
| Ciprofloxacin 1.0 | 100 | 0 |
| Negative-Meat | 100 | 0 |
| Enrofloxacin 30 | 0 | 100 |
| Enrofloxacin 15 | 10 | 90 |

EXAMPLE 3

Lateral Flow Test for Aflatoxin in milk, feed, corn, peanut extract

Construction of the aflatoxin test device are common with the beta-lactam lateral flow device. Some modifications are required for adapting the assay to various matrices e.g. milk, feed extracts etc.

The lateral flow test for aflatoxin includes: a test zone made of BSA-aflatoxin conjugate, a control zone made of Goat Anti-Rabbit IgG, and a mobile phase made of Anti-aflatoxin antibodies—Gold conjugate.

Mobile Phase Construction.

Broad spectrum Rabbit anti aflatoxin antibodies are prepared using protein A affinity chromatography. The preferred antibodies are those with good cross reactivity to aflatoxin B1, M1, G1, B2, G2.

Colloidal gold 10 to 50 nm are prepared at 2 $OD_{540}$ and coated with precalibrated amount of purified antibodies as described for the tetracycline test. The colloidal gold beads are further stabilized with 1% bovine serum albumin, washed twice in 2mM Borax/1% BSA and concentrated to about 30 $OD_{540}$ with glycerol (final concentration of 30%). They can be kept at −20° C. for at least one year.

For spraying, the antibody coated Gold beads are suspended in a solution containing protein e.g. albumin bovine (BSA) at 10%, sucrose at 40% or polyethylene glycol 3550 MW at 10 to 40% and sprayed in pretreated mobile support phase as a 5 mm band at about 1/cm. The mobile support phase is then dried at 37 to 55° C. for 16 to 2 hours respectively.

Pre-treated mobile-support

Mobile-support phase strips are soaked (50 strips per liter) for 2 hours in a solution of: 0.5% BSA, 0.5% sucrose, 0.5% Tween 20, 0.01% SDS, and 2 mM Borax.

Excess solution is removed by dripping and strips are hanged horizontally at 55° C. for drying at least 4 hours and preferred overnight.

Stationary Phase—Test Zone

Aflatoxin B1 is chemically attached to BSA or OVA or other protein. The objective is a ratio of 2 to 10 moles of aflatoxin B1to mole BSA. The BSA-aflatoxin B1 conjugate is then mixed with carrier protein (0.1 to 2%) and sugar or PEG (1 to 5%) or glycerol (10 to 30%) and kept at −20° C. The conjugate solution is applied to the nitrocellulose strip at 0.5 to 2 μl/cm (or 2–20 ng total Aflatoxin B1 per cm). Heat treatment of the membrane at 55° C. stabilizes the test zone construction. This creates a stationary phase with a molecular sieve that efficiently interact and capture aflatoxin free anti-aflatoxin tagged gold—beads. During the test, the sugar and/or PEG and/or glycerol in the test zone are dissolved by the advancing sample fluid leaving a porous 3D type structure with highly effective analyte sites to bind the antibodies tagged gold beads.

Control Zone —Reference Zone

A pure Goat anti-rabbit IgG is immobilized as a line parallel to the test zone. The Goat anti rabbit IgG is applied to the nitrocellulose in similar solutions as the test zone at precalibrated concentration of 1 to 10% to create binding sieve of the anti aflatoxin tagged gold beads equivalent to the test zone. This zone captures anti-aflatoxin tagged gold beads regardless of presence of lack of bound aflatoxin.

Matrices:

Milk: Homogenized and Raw milk can be tested directly in the device at 35 to 55° C. Grain, nuts, Feed Testing: For example 50 gm corn is homogenized in 100 ml 80% methanol. The extract is filtered, centrifuged or let stand for 10 minutes to clarify. The extract is then diluted 1 to 7 in a buffer, containing 25 mM phosphates pH7.4 and 2% bovine serum albumin or milk powder. Sample of 0.3 ml of diluted extract is added to the lateral flow device. Assay develops at 45 ° C. within 3 to 8 minutes.

TABLE 4

Test Performance for Aflatoxin

| Toxin levels (in ppb) | Estimated % Negative | Estimated % Positive |
|---|---|---|
| Negative - FEED | 100 | 0 |
| Aflatoxin B1 30 | 0 | 100 |
| Aflatoxin B1 20 | 0 | 100 |
| Aflatoxin B1 10 | 0 | 100 |
| Aflatoxin B1 5 | 70 | 30 |
| Aflatoxin B1 1 | 0 | 100 |
| Negative - MILK | 100 | 0 |
| Aflatoxin M1 0.5 | 100 | 0 |
| Aflatoxin M1 0.25 | 100 | 0 |
| Aflatoxin M1 0.1 | 60 | 40 |

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An inhibition-type assay test device for detecting the presence of one or more members of an analyte family, wherein a positive result does not differentiate one particular analyte from another, at reduced sensitivity safe levels in an analyte family, in a sample, which test device comprises:
    a) a mobile-phase composition having a labelled receptor for binding with all of the members of an analyte family and one or more analyte specific antibodies, each analyte specific antibody having a binding affinity for a selected analyte of the analyte family, but not all of the analyte family; the analyte specific antibody competing with the labelled receptor to remove a specific analyte from binding to said labelled receptor which is capable of binding to a family of analytes; the analyte specific antibodies present in an amount to reduce the test sensitivity for the selected analyte; and which analyte specific antibodies do not compete for binding at the test zone or control zone, but pass unreacted through the test zone and control zone toward a disposal zone;
    b) a stationary-phase membrane in contact or contacted with the mobile-phase composition and having a first end and a second end, and wherein said membrane allows lateral capillary flow of the sample from the first end to the second end;
    c) a test zone on the membrane having a first binder bound to said membrane, said first binder bound to said membrane containing an analyte member of the analyte family, to form a first analyte-labelled receptor complex, other than an analyte for which there is provided an analyte specific antibody, and said first binder binding with unbound labelled receptor to provide a detectable signal; and
    d) a control zone having a second binder bound to said membrane to bind with said labelled receptor, to provide a signal that the test is complete, and for comparison to the signal of the test zone; the test device arranged and constructed to provide a positive or negative result of the safe threshold level of the analyte family present, where each member has a threshold for a positive or negative result, which is different from other members.

2. The test device of claim 1 wherein said analyte specific antibody is selected from the group consisting of the antibodies for cephapirin, ampicillin, ceftiofur and amoxicillin.

3. The test device of claim 1 wherein said device further includes a second test zone for detecting additional analytes or analyte families between the first test zone and the control zone.

4. The test device of claim 1 wherein said device further includes a third test zone for detecting additional analytes or analyte families between the first test zone and the control zone.

5. The device of claim 1 wherein the labelled receptor comprises a receptor bound to visible microparticles.

6. The device of claim 1 wherein the labelled receptor comprises protein-coated, gold microsphere beads.

7. The device of claim 1 wherein the test device is for the detection of cephapirin at a sensitivity of about 15 to 20 ppb.

8. The device of claim 1 wherein the test device is for the detection of ceftiofur at a sensitivity of about 40 to 50 ppb.

9. The device of claim 1 wherein the mobile-phase composition includes a protein or polyclonal antibody for the analyte or analyte family and an attached mobile visible marker.

10. The device of claim 1 wherein said device detects an analyte or analyte family selected from the group consisting of; toxins; beta-lactams; tetracyclines; sulfonamides; macrolides; aminoglycosides; quinolones; pesticides; and microorganisms.

11. The device of claim 1 wherein said device detects a beta-lactam selected from the group consisting of: penicillin; ampicillin; amoxicillin; cloxacillin; dicloxacillin; oxacillin; certiofur; and cephapirin.

12. The device of claim 1 wherein said device detects a tetracycline selected from the group consisting of: chlortetracycline; oxytetracycline; and tetracycline.

13. The device of claim 1 wherein said device detects a sulfonamide selected from the group consisting of: sulfamethazine; sulfadimethoxine; sulfamerazine; sulfathiazole; and sulfadiazine.

14. The device of claim 1 wherein said device detects a macrolide selected from the group consisting of: erythromycin; spiramycin; and tylosin.

15. The device of claim 1 wherein said device detects an aminoglycoside selected from the group consisting of: gentamicin; neomycin; and DH/streptomycin.

16. The device of claim 1 wherein said device detects a quinoline selected from the group consisting of: eurofloxacin; dorfloxacin; ciprofloxacin; and sarafloxacin.

17. The device of claim 1 wherein said mobile-phase composition includes a salt.

18. The device claim 17 wherein said salt includes a citrate.

19. An inhibition-type assay test device for detecting the presence of one or more members of an analyte family, wherein a positive result does not differentiate one particular analyte from another, at reduced sensitivity safe levels in an analyte family, in a sample, which test device comprises:
    a) a support strip;
    b) a sample-absorbing matrix attached to said support strip, said sample-absorbing matrix having material for absorbing an amount of the sample;
    c) a mobile-phase support for holding a mobile-phase composition, said mobile-phase support and mobile-phase composition being in contact with said sample-absorbing matrix;

d) a mobile-phase composition having a labelled receptor for binding with all of the members of an analyte family and one or more analyte specific antibodies, each analyte specific antibody having a binding affinity for a selected analyte of the analyte family, but not all of the analyte family; the analyte specific antibody competing with the labelled receptor to remove a specific analyte from binding to said labelled receptor which is capable of binding to a family of analytes; the analyte specific antibodies present in an amount to reduce the test sensitivity for the selected analyte; and which analyte specific antibodies do not compete for binding at the test zone or control zone, but pass unreacted through the test zone and control zone toward a disposal zone;

e) a stationary-phase membrane in contact or contacted with the mobile-phase composition and having a first end and a second end, and wherein said membrane allows lateral capillary flow of the sample from the first end to the second end;

f) a test zone on the membrane having a first binder bound to said membrane, said first binder bound to said membrane containing an analyte member of the analyte family, to form a first analyte-labelled receptor complex, other than an analyte for which there is provided an analyte specific antibody, and said first binder binding with unbound labelled receptor to provide a detectable signal; and g) a control zone having a second binder bound to said membrane to bind with said labelled receptor, to provide a signal that the test is complete, and for comparison to the signal of the test zone; the test device arranged and constructed to provide a positive or negative result of the safe threshold level of the analyte family present, where each member has a threshold for a positive or negative result, which is different from other members.

20. The device of claim 19 wherein the test device comprises a test strip on the support strip having a liquid sample-absorbing matrix and the test strip is within a transparent, elongated blister housing.

21. The device of claim 20 wherein the elongated blister housing comprises a transparent plastic blister housing adhesively secured to a tape strip and having a peelable end tab to expose the sample-absorbing matrix to a liquid sample.

22. The device of claim 21 wherein the elongated blister housing includes an expansion cavity at the one end of the housing and opposite to the sample-absorbing matrix, to permit selected expansion of the sample-absorbing matrix to fill the expansion cavity.

23. The device of claim 19 wherein said device further includes an elongate blister housing enclosing said support strip, sample-absorbing matrix, mobile-phase support, mobile-phase composition, stationary-phase membrane, test zone and control zone, said elongate blister housing defining an elongated strip cavity having a first end and a second end.

24. The device of claim 23 wherein said elongate blister housing includes a transparent, top-cover section to allow observation of test results on the test device.

25. The device of claim 24 wherein said elongate blister housing is characterized by an expansion cavity housing at the one end and extending outwardly from a top cover.

26. The device of claim 25 wherein the sample-absorbing matrix includes a generally rectangular material which expands upon contact with the liquid sample, to fill a rectangular-shaped expansion cavity housing having a slanted top housing wall to direct the liquid sample toward the other end.

27. The device of claim 25 wherein the expansion cavity includes a top cover which has one or more apertures therein, to increase the penetration efficiency of the liquid sample into the sample-absorbing sponge.

28. The device of claim 23 wherein the elongate blister housing is formed of a transparent plastic material.

29. The device of claim 23 wherein the first end includes a means to seal an expansion cavity housing, which includes an end cap or peel strip which fits over or seals an end of the expansion cavity.

30. The device of claim 23 wherein the elongate blister housing includes a transparent, plastic blister housing sealed by a tape strip and includes a peelable tab at the first end.

31. A test system which includes an incubator for the insertion of the test device in an incubation cavity and the test device of claim 23.

32. The device of claim 19 wherein the sample-absorbing matrix includes a dry, compressed, cellulosic-membrane material.

33. The device of claim 19 wherein said device further includes a disposal zone at the second membrane end for absorbing an excess amount of said sample.

* * * * *

UNITED STATES PATENT AND TRADEMARK OFFICE
CERTIFICATE OF CORRECTION

PATENT NO. : 6,319,466 B1
DATED : November 20, 2001
INVENTOR(S) : Markovsky et al.

It is certified that error appears in the above-identified patent and that said Letters Patent is hereby corrected as shown below:

<u>Title page,</u>
Item [63], Related U.S. Application Data, please replace the existing paragraph with the following:
-- Provisional application No. 60/052,644, filed on Jul. 16, 1997, and provisional application No. 60/088,937, filed on Jun. 11, 1998. --

Signed and Sealed this

Fourth Day of November, 2003

JAMES E. ROGAN
*Director of the United States Patent and Trademark Office*